United States Patent [19]

Canto et al.

[11] 4,018,651

[45] Apr. 19, 1977

[54] METHOD FOR REGENERATING GLUCOSE OXIDASE REAGENT

[76] Inventors: Elio D. Canto, 425 W. 205th St., New York, N.Y. 10034; Albert H. Padovani, Orchard Hill Road, Katonah, N.Y. 10536

[22] Filed: Mar. 20, 1975

[21] Appl. No.: 560,231

[52] U.S. Cl. .......................................... 195/103.5 C
[51] Int. Cl.² .......................................... G01N 31/14
[58] Field of Search .............. 195/103.5 C, 103.5 R

[56] References Cited

UNITED STATES PATENTS

| 3,677,903 | 7/1972 | Bittner | 195/103.5 R |
| 3,838,011 | 9/1974 | Hagen et al. | 195/103.5 R |
| 3,857,771 | 12/1974 | Steinberg | 195/103.5 R |

OTHER PUBLICATIONS

Aebi, "Catalase," Method of Enzymatic Analysis by H. H. Bergmeyer, Academic Press, Inc., 2nd Ed., (1974), vol. 2, pp. 673–674.

*Primary Examiner*—Alvin E. Tanenholtz
*Assistant Examiner*—C. A. Fan

[57] ABSTRACT

A glucose oxidase reagent used in an instrumental analyzer, wherein glucose concentration is determined as directly proportional to the rate of oxygen comsumption by glucose in a sample of a biological fluid, is regenerated by mixing and collecting the used reagent in a waste bottle containing sufficient catalase to provide a concentration of at least 2 U/ml of catalase in the total amount of waste liquid. A new glucose oxidase reagent formulation is also provided which contains at least 90 U/ml of catalase and can be continuously recycled by passing the used reagent directly back into the fresh reagent without first collecting in a waste bottle.

9 Claims, No Drawings

METHOD FOR REGENERATING GLUCOSE OXIDASE REAGENT

BACKGROUND OF THE INVENTION

The present invention relates to methods for analysis of glucose in biological fluids, especially blood plasma or serum, or in aerated urine. More particularly this invention relates to methods for regenerating the glucose oxidase reagent used in instrumental analyzers for determining glucose concentration, such as the Beckman Glucose Analyzer. Such analyzers are discussed in U.S. Pat. No. 3,765,841, column 2, line 44 ff.

In the Beckman Glucose Analyzer, glucose is determined by treating the sample containing glucose with an aerated enzyme reagent containing glucose oxidase and measuring the rate of resultant oxygen consumption. The oxygen content is measured by a sensor which responds to oxygen concentration. Solid-state electronic circuitry determines the rate of oxygen consumption, which is directly proportional to the concentration of glucose in the sample. The latter is indicated on the analyzer by direct readout in milligrams of glucose per 100 ml. of sample.

The Beckman glucose oxidase reagent consists of 150EU/ml of glucose oxidase (*Aspergillus niger*) in 5% denatured ethanol $10^{-2}$ M potassium iodide solution. The reagent also contains catalase, which occurs as a natural impurity in glucose oxidase, and ammonium molybdate as catalytic reagents prepared in a phosphate buffer with $5 \times 10^{-4}$ iodine as a preservative.

When a biological sample containing glucose is injected into the aerated enzyme reagent solution, β-D-glucose from the sample combines with dissolved oxygen from the solution according to the reaction:

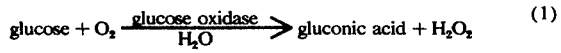

(1)

In the above reaction the oxygen is consumed at the same rate as the glucose reacts.

Because oxygen consumption rather than peroxide formation is measured, the only requirement for peroxide is that it must be destroyed by a path not leading back to oxygen. The ethanol present in the reagent causes the $H_2O_2$ to be destroyed by catalase, an impurity in the glucose oxidase, without yielding oxygen in accordance with the reaction:

(2)

To ensure destruction of the peroxide, iodide and molybdate are added to the enzyme reagent, causing the reaction

(3)

This reaction is effective even after catalase activity has diminished with storage.

Before analyses are performed in the Beckman Glucose Analyzer, the enzyme reagent must be aerated by shaking in the bottle several times with fresh portions of air. The aeration is necessary in order to provide the oxygen to react with the glucose according to equation (1).

A bottle of 250 ml. of enzyme reagent is used in the glucose analyzer and is sufficient for 250 glucose tests. In other words, 1 ml. of the enzyme reagent is conveyed to a sample cup for each test to be performed. The amount of sample analyzed in each test is 10 µl. At the conclusion of each test, the contents of the sample cup are drained into a waste bottle. When all of the used enzyme reagent (including the tested samples) has been collected in the waste bottle, it is discarded and a new bottle of enzyme reagent placed in the analyzer.

DESCRIPTION OF THE INVENTION

The invention relates to an improvement in the method for determining the concentration of glucose in a sample of biological fluid, such as blood plasma or serum, spinal fluid or urine wherein the sample containing glucose is introduced into an aerated reagent comprising glucose oxidase, catalase and ethanol; the glucose reacts with oxygen present in the aerated reagent; the rate of oxygen consumption is measured; the concentration of glucose is calculated, said concentration being proportional to the rate of oxygen consumption; and the waste liquid comprising the sample and used reagent is collected in a waste container. The improvement comprises adding to the waste container prior to collection of waste liquid therein, an amount of catalase sufficient to provide a concentration of at least 2 U/ml, preferably 3–4 U/ml of catalase in the total volume of waste liquid. After the total volume of waste liquid has been collected, it is aerated and then reused as the reagent for additional determinations of glucose concentration according to the same method.

Thus, the waste reagent does not need to be discarded but can be reused for another series of tests. This procedure can be repeated numerous times, as long as the catalase is added each time to the empty waste bottle prior to collection of the waste reagent. Surprisingly, addition of the catalase to the already collected waste reagent does not have the same effect and the reagent cannot be recycled. The amount of catalase added to the waste bottle should be sufficient to provide a concentration of at least 2 U/ml. preferably 3–4 U/ml of catalase in the total amount of waste liquid collected.

Using the method of the invention, at least 13,500 tests can be run from one 250 ml. bottle of glucose oxidase reagent, originally intended for 250 tests by recycling 54 times. Since the cost of the reagent activator required for the 54 recycles is much less than the cost of 54 bottles of fresh reagent, this represents a tremendous economic advantage.

The catalase which is added to the waste bottle may be pure catalase. However, since catalase occurs as a natural impurity in glucose oxidase, obtained from *Aspergillus niger* it may also be added in this form combined with the glucose oxidase. An amount of glucose oxidase providing 100 EU/ml in the collected waste liquid will provide approximately 2 catalase units/ml. This is the minimum amount for operability but some accuracy is sacrificed. A satisfactory range can be obtained from 150 EU/ml. of glucose oxidase providing approximately 3 catalase units/ml. The optimum range is from 200 to 300 EU/ml of glucose oxidase providing 3–4 catalase units/ml. It has been found that as much as 50,000 EU/ml of glucose oxidase, containing approximately 600 catalase units/ml may be used.

Additional catalase can be used as a preservative to insure glucose oxidase reagent activity for a long period of time and/or many glucose tests. For example, 1 ml. of 90 U/ml of catalase may be added to the collection bottle per each 25 ml. of glucose oxidase reagent. Best results are obtained using 90 U/ml of catalase and 200 EU/ml of glucose oxidase reagent.

Since the amount of glucose oxidase and/or catalase added to the waste bottle is very small, the preferred method is to mix it with a small amount of distilled water or particularly fresh or regenerated reagent in the waste bottle to avoid evaporation or physical loss. For example, if glucose oxidase obtained from *Aspergillus niger* having an activity of approximately 4000 EU/ml. is used as the reagent activator, 0.25 ml. is employed per 250 ml. of reagent to be regenerated. Therefore, about 10 ml. of fresh or regenerated reagent is placed in the waste bottle to which the 0.25 ml. of reagent activator is added.

A unit of glucose oxidase is that amount of enzyme which causes the oxidation of 1.0 $\mu$M of glucose to gluconic acid per minute at pH 5.1 at 35° C. (equivalent to an oxygen uptake of 22.4 uL/minute).

The procedure to follow using the commercially available Beckman Glucose Analyzer and a reagent activator containing both glucose oxidase and catalase is as follows:

1. Open a new bottle of Beckman Glucose Analyzer Reagent (150 EU/ml glucose oxidase) previously stored in the temperature-controlled reagent compartment of the Beckman Glucose Analyzer.
2. Follow aeration procedures as indicated in the Beckman Glucose Analyzer operating manual.
3. Mix 1 ml. of reagent activator (activity 200 EU/ml glucose oxidase and 90 U/ml catalase) with approximately 10 ml. of the Beckman Glucose Analyzer Reagent and deliver it into the waste bottle.
4. Start using the Beckman Glucose Analyzer as indicated in the Operating Manual.
5. When only about 10 ml. of the Glucose Analyzer Reagent remains in the reagent bottle, transfer the contents of the waste bottle to the reagent bottle and repeat steps (2)–(5) every time the reagent bottle is emptied. When the original reagent has been used 48 times (12,000 tests), one addition of reagent activator (R/A) can be skipped every 500 tests; 12,500 + 0.25 ml R/A; 13,000 + 0.25 ml R/A; 13,500 + 0.25 ml R/A. A total of 12.0 ml. of R/A will have been used for recycling the original reagent 54 times.

It appears that the older the reagent gets, the better it works.

As stated previously, the Beckman Glucose Analyzer Reagent, designed specifically for use with the Beckman Glucose Analyzer, consists of 150 U/ml. of glucose oxidase (*Aspergillus niger*), containing catalase as impurity, in 5% denatured ethanol $10^{-2}$M KI solution containing ammonium molybdate, phosphate buffer and $5 \times 10^{-4}$ m iodine as preservative. Variations on the above reagent are possible such as the following formulations:

No. 1.
 A. Iodine 0.01 N to 0.10 N, optimum 0.05N
 B. Glucose Oxidase (A. niger) 100–4000 EU/ml, optimum 200 EU/ml
 C. Denatured Ethanol 2–10%, optimum 5%
 D. Additional catalase 9–900 U/ml. optimum 90 U/ml No. 2.
 A. Glucose Oxidase (A. Niger) 160 EU/ml
 B. Distilled water
 C. 5% Denatured ethanol No. 3.
 A. Glucose Oxidase (A. Niger) 160 EU/ml.—(10 ml.)
 B. Catalase solution 90 U/ml.—(227.5 ml.)
 C. 5% Denatured ethanol—(12.5 ml. ethanol)

These formulations may also be regenerated and reused according to the invention.

Formulation No. 3 is of particular utility and represents another aspect of the invention. It has been found that this reagent may be continuously recycled without further additions of catalase, as is necessary with Formulations No. 1 and No. 2 and the Beckman Reagent. Although Formulation No. 3 represents the preferred concentrations of the three essential components, it has been found that the operable ranges are as follows:

A. Glucose Oxidase (A. Niger) 100–4000 EU/ml
 B. Additional Catalase 90–900 U/ml
 C. Denatured ethanol 2–10%.

In order to recycle this reagent continuously, the normal operating procedure for the Beckman Glucose Analyzer is modified. Instead of drawing off the used reagent and sample from each test into a waste bottle, the waste is passed directly back to the reagent bottle by placing the drain tube from the sample cup into the reagent bottle, thus eliminating the separate step of waste collection and shut-down of the machine to recycle the waste. It has been found that 250 ml. of Formulation No. 3 reagent according to the invention can be used for at least 15,000 tests without loss of accuracy, which amounts to 2–5%.

We claim:

1. In a method for determining the concentration of glucose in a sample of biological fluid wherein the sample containing glucose is introduced into an aerated reagent comprising glucose oxidase, catalase, and ethanol; the glucose reacts with oxygen present in the aerated reagent; the rate of oxygen consumption is measured; the concentration of glucose is calculated, said concentration being proportional to the rate of oxygen consumption; and the waste liquid comprising the sample and used reagent is collected in a waste container, the improvement which comprises adding to said waste container prior to collection of waste liquid therein, a reagent activator comprising an amount of catalase sufficient to provide a concentration of at least 2 U/ml of added catalase in the total volume of waste liquid collected, aerating the thus treated waste liquid and using said treated aerated waste liquid as the reagent for additional determinations of glucose concentration according to said method.

2. The improvement according to claim 1 wherein the catalase concentration is at least 3 to 4 U/ml in said treated waste liquid.

3. The improvement according to claim 1 wherein the reagent activator is in the form of impure glucose oxidase which contains catalase as an impurity.

4. The improvement according to claim 1 wherein the added catalase is pure catalase.

5. The improvement according to claim 1 wherein the reagent activator provides an amount of 900 U of added catalase and 2000EU of added glucose oxidase per 250 ml. of waste liquid collected.

6. An enzyme reagent for determining the concentration of glucose in a sample by measuring the rate of oxygen consumption by said glucose in the presence of said enzyme wherein said rate is proportional to said concentration of glucose, said reagent consisting of an aqueous ethanol solution containing from 2–10% ethanol, from 100–4000 EU/ml. of glucose oxidase and from 90–900 U/ml. of catalase in addition to any catalase which may be present as an impurity in the glucose oxidase.

7. An enzyme reagent according to claim 6 which consists of an aqueous ethanol solution containing 5% ethanol, 160 EU/ml of glucose oxidase and 90 U/ml of catalase.

8. In a method for determining the concentration of glucose in a biological fluid wherein a portion of an aerated glucose oxidase reagent is transferred from a reagent reservoir to a reaction chamber, the sample containing glucose is introduced into said reaction chamber; the glucose reacts with oxygen present in the aerated reagent; the rate of oxygen consumption is measured; and the concentration of glucose is calculated, said concentration being proportional to the rate of oxygen consumption the improvement wherein the reagent is the reagent according to claim 6 and the mixture of sample and used reagent is continuously recycled to the reservoir.

9. The method of claim 8 wherein the reagent consists of an aqueous ethanol solution containing 5% ethanol, 160 EU/ml. of glucose oxidase and 90 U/ml. of catalase.

* * * * *